(12) United States Patent
Ho et al.

(10) Patent No.: US 8,439,974 B2
(45) Date of Patent: May 14, 2013

(54) ADJUSTED INDEX OF REFRACTION OF OCULAR REPLACEMENT MATERIAL

(75) Inventors: Arthur Ho, New South Wales (AU); Brien Anthony Holden, New South Wales (AU); Fabrice Manns, Palmetto Bay, FL (US); Jean-Marie Arthur Parel, Miami Shores, FL (US)

(73) Assignee: Vision CRC Limited, Kensington, New South Wales (AU)

( * ) Notice: Subject to any disclaimer, the term of this patent is extended or adjusted under 35 U.S.C. 154(b) by 692 days.

(21) Appl. No.: 12/299,239

(22) PCT Filed: May 3, 2007

(86) PCT No.: PCT/AU2007/000586
§ 371 (c)(1),
(2), (4) Date: Oct. 31, 2008

(87) PCT Pub. No.: WO2007/128055
PCT Pub. Date: Nov. 15, 2007

(65) Prior Publication Data
US 2009/0076602 A1    Mar. 19, 2009

Related U.S. Application Data

(60) Provisional application No. 60/796,940, filed on May 3, 2006.

(51) Int. Cl.
*A61F 2/16*    (2006.01)
(52) U.S. Cl.
USPC ........................................ 623/6.56; 623/6.11

(58) Field of Classification Search ................ 623/6.56
See application file for complete search history.

(56) References Cited

U.S. PATENT DOCUMENTS

| | | | |
|---|---|---|---|
| 4,136,250 A | 1/1979 | Mueller |
| 4,486,577 A | 12/1984 | Mueller |
| 4,542,542 A | 9/1985 | Wright |
| 4,563,539 A | 1/1986 | Gornowicz |
| 4,605,712 A | 8/1986 | Mueller |

(Continued)

FOREIGN PATENT DOCUMENTS

| | | |
|---|---|---|
| DE | 19649844 | 2/1996 |
| EP | 0293560 | 12/1988 |

(Continued)

OTHER PUBLICATIONS

Dubbelman, M. et al (2001) "The thickness of the aging human lens obtained from correct scheimpflug images," Optometry and Vision Science; 2001; 78(6): 411.

(Continued)

*Primary Examiner* — Corrine M McDermott
*Assistant Examiner* — Randy Shay
(74) *Attorney, Agent, or Firm* — Foley & Lardner LLP (57) ABSTRACT

The present invention relates to a method of determining the IOL refractive index for an ocular replacement material for replacing tissue in the capsular bag comprising combining a neutral (non-correcting) reference refractive index ("NRRI") of between 1.421 and 1.450 with a refractive index correction factor ("RICF") ascertained by reference to the refractive power required to correct the patient's refractive error. The present invention also relates to methods of treating presbyopia, myopia and hyperopia using the above method.

18 Claims, 6 Drawing Sheets

U.S. PATENT DOCUMENTS

| | | | |
|---|---|---|---|
| 4,616,045 A | 10/1986 | Upchurch | |
| 4,852,969 A | 8/1989 | Babirad | |
| 5,079,319 A | 1/1992 | Mueller | |
| 5,116,369 A | 5/1992 | Kusibiki | |
| 5,225,858 A * | 7/1993 | Portney | 351/161 |
| 5,233,007 A | 8/1993 | Yang | |
| 5,236,970 A | 8/1993 | Christ | |
| 5,246,979 A | 9/1993 | Lutz | |
| 5,278,258 A | 1/1994 | Gerace | |
| 5,346,946 A | 9/1994 | Yokoyama | |
| 5,376,694 A | 12/1994 | Christ | |
| 5,391,590 A | 2/1995 | Gerace | |
| 5,397,848 A | 3/1995 | Yang | |
| 5,411,553 A | 5/1995 | Gerace | |
| 5,420,213 A | 5/1995 | Yang | |
| 5,444,106 A | 8/1995 | Zhou | |
| 5,476,515 A | 12/1995 | Kelman | |
| 5,494,946 A | 2/1996 | Christ | |
| 5,556,383 A | 9/1996 | Wang | |
| 5,610,257 A | 3/1997 | Richard | |
| 5,647,409 A | 7/1997 | Christ | |
| 5,661,195 A | 8/1997 | Christ | |
| 5,772,667 A | 6/1998 | Blake | |
| 5,869,549 A | 2/1999 | Christ | |
| 5,977,282 A | 11/1999 | Ebbrecht | |
| 5,981,615 A | 11/1999 | Meigs | |
| 6,066,172 A | 5/2000 | Huo et al. | |
| 6,277,147 B1 | 8/2001 | Christ | |
| 6,361,561 B1 | 3/2002 | Huo | |
| 6,399,734 B1 | 6/2002 | Hodd | |
| 6,432,137 B1 | 8/2002 | Nanushyan | |
| 6,589,550 B1 | 7/2003 | Hodd | |
| 6,663,668 B1 | 12/2003 | Chaouk | |
| 6,747,090 B2 | 6/2004 | DeGroot | |
| 7,060,095 B2 | 6/2006 | Ho et al. | |
| 7,348,022 B1 | 3/2008 | Clayton | |
| 2002/0082691 A1 | 6/2002 | Christ | |
| 2004/0054026 A1 | 3/2004 | Kunzler | |
| 2004/0116593 A1 | 6/2004 | Lai | |
| 2004/0156880 A1 | 8/2004 | Ravi | |
| 2005/0004255 A1 | 1/2005 | Clayton | |
| 2005/0038219 A1 | 2/2005 | Lai | |
| 2005/0054802 A1 | 3/2005 | Lai | |
| 2005/0070626 A1 | 3/2005 | Lowery | |
| 2005/0203619 A1 * | 9/2005 | Altmann | 623/6.23 |
| 2005/0228120 A1 | 10/2005 | Hughes | |
| 2006/0106458 A1 * | 5/2006 | Jason et al. | 623/6.11 |
| 2006/0135477 A1 | 6/2006 | Haitjema et al. | |

FOREIGN PATENT DOCUMENTS

| | | |
|---|---|---|
| EP | 0335312 | 10/1989 |
| EP | 0578087 | 1/1994 |
| EP | 1176454 | 1/2002 |
| JP | 2002-128829 | 5/2002 |
| WO | WO 93/21245 | 10/1993 |
| WO | WO 99/47185 | 9/1999 |
| WO | WO 00/22459 | 4/2000 |
| WO | WO 00/22460 | 4/2000 |
| WO | WO 01/08603 | 2/2001 |
| WO | WO 01/17570 | 3/2001 |
| WO | WO 01/76651 | 10/2001 |
| WO | WO 01/81075 | 11/2001 |
| WO | WO-01/89435 | 11/2001 |
| WO | WO 01/89435 | 11/2001 |
| WO | WO 03/009014 | 1/2003 |
| WO | WO 03/040154 | 5/2003 |
| WO | WO 03/040155 | 5/2003 |
| WO | WO 03/066707 | 8/2003 |
| WO | WO-2004/011529 | 2/2004 |
| WO | WO 2004/011529 | 2/2004 |
| WO | WO 2004/049979 | 6/2004 |
| WO | WO 2005/023331 | 3/2005 |
| WO | WO 2007/078585 | 12/2007 |

OTHER PUBLICATIONS

Dubbelman, M. et al "The shape of the aging human lens: curvature, equivalent refractive index and the lens paradox"; Vision Research; 2001; 41: 1867.

Escudero-Sanz, I. and Navarro, R. "Off-axis aberrations of a wide-angle schematic eye model"; J. Opt. Soc. Am. A; 1999; 16(8): 1881.

Fisher, R.F. et al "The elastic constants of the human lens" J Physiology, 1971; 212; pp. 147-180.

Jones, C. E. et al "Refractive index distribution and optical properties of the isolated human lens measured using magnetic resonance imaging (MRI)"; Vision Research; 2005; 45; 2352.

Heys, K.R. et al "Massive increase in the stiffness of the human lens nucleus with age: the basis for presbyopia?" Molecular Vision; Nov. 17, 2004; vol. 10; pp. 956-963.

Nishi, O. and Nishi, K. "Accomodation amplitude after lens refilling with injectable silicone by sealing the capsule with a plug in primates"; Arch Ophthalmol; 1998; 116: 1358.

Phan-Thien, N. et al "Micro-Fourier rheometer: Inertial effects" Rheol Acta; 1996; vol. 35; pp. 410-416.

Pierscionek, B. K. et al "Refractive Index Gradient of Human Lenses"; Optometry and Vision Science; 1989; 66 (12): 822.

Pierscionek, B. K. (1997) "Refractive Index Contours in the Human Lens"; Exp. Eye Res.; 1997; 64: 887.

Schachar, R.A. et al "Viscoelastic shear properties of the fresh porcine lens" Br J Ophthalmol; 2007; vol. 91; pp. 366-368.

Siedlecki, D. et al "Schematic eye with a gradient-index lens and aspheric surfaces"; Optics Letters; 2004; 29(11): 1197.

Smith, G. et al "The optical modelling of the human lens"; Ophthal. Physiol. Opt.; 1991; 11(4): 359.

Smith, G. et al "Modeling the power of the aging human eye"; J. Opt. Soc. Am. A; 1992; 9 (12): 2111.

Smith, G. and Pierscionek, B. K. "The optical structure of the lens and its contribution to the refractive status of the eye"; Ophthal. Physiol. Opt.; 1998; 18(1): 21.

Weber, H.A. et al "Dynamic mechanical properties of human lenses" Experimental Eye Research; 2005; vol. 80: 425-434.

Zelentsova, N.V., Zelentsov, S.V., Abadie, M.J.M. and Makareeva, N. "Photochemical crosslinking of the low molecular weight vinyl containing polysiloxanes with organic azides"; Phobiology 2002.

Ziebarth, N.M. et al "Atomic force microscopy measurements of lens elasticity in monkey eyes" Molecular Vision; 2007; vol. 13; pp. 504-510.

Ho et al., "Presentation 5891," slide presentation, ARVO Meeting, Fort Lauderdale, Florida, May 2, 2006.

Manns et al., "Optomechanical response of normal and refilled lenses in a lens stretcher," slide presentation, Accommodation Club Meeting, Miami, Florida, May 5, 2006.

Ho et al., "Lens Refilling Results in the Live Monkey Model," slide presenatation, Accommodation Club Meeting, Miami, Florida, May 5, 2006.

Hughes et al., "In situ curable accommodating implant," slide presentation, 28th Australasian Polymer Symposium, Rotorua, New Zealand, Feb. 5-9, 2006.

Instron, "Modulus of Elasticity: Glossary of Material Testing Terms," http://www.instron.us/wa/resourcecenter/glossaryterm.aspx?ID=99, obtained Apr. 10, 2008.

Ho et al., "Theoretical Analysis of Accommodation Amplitude and Ametropia Correction by Varying Refractive Index in Phaco-Ersatz," *Optometry and Vision Science*, vol. 78, No. 6, pp. 405-410, Jun. 2001.

* cited by examiner

ADJUSTED INDEX OF REFRACTION OF OCULAR REPLACEMENT MATERIAL

FIELD OF THE INVENTION

The invention relates to a new eye treatment including the replacement of the lens of an eye with an artificial accommodating intraocular lens. It can be used, for example, to treat presbyopia.

BACKGROUND OF THE INVENTION

The human eye is a complex sensory organ. It includes a cornea, or clear outer tissue which refracts light rays en route to the pupil, an iris which controls the size of the pupil thus regulating the amount of light entering the eye, and a lens which focuses the incoming light through the vitreous to the retina. The lens is often considered to have 3 portions, namely a nucleus, a cortex around the nucleus and an outer capsular region. In the adult lens, the nucleus tends to be harder and has a relatively constant sectional refractive index, whereas the refractive index of the cortex is known to exhibit a gradient. Any obstruction or loss in clarity within these structures causes scattering or absorption of light rays resulting in diminished vision.

With age, there is a loss of lens flexibility and/or lens transparency. The natural flexibility of the lens is essential for focusing light onto the retina by a process referred to as accommodation. Accommodation is the process by which the eye adjusts its focus for visual objects at different distances. A common condition known as presbyopia results from diminished flexibility of the lens thus reducing near vision acuity. Presbyopia usually begins to occur in adults during their mid-forties; conventionally, these near vision problems are alleviated with glasses or contact lenses.

Another cause of diminished vision is cataracts which is associated with a loss of lens transparency in the aging eye. Some treatments involve the surgical removal of the natural lens. An artificial lens is then needed to restore vision. Three types of prosthetic lenses are available: cataract glasses, external contact lenses, and IOLs. Cataract glasses have thick lenses, are uncomfortably heavy, and cause vision artifacts such as central image magnification and side vision distortion. Contact lenses resolve many of the problems associated with glasses, but require cleaning, are difficult to handle (especially for elderly patients with symptoms of arthritis), and are not suited for persons who have restricted tear production. More particularly, contact lens for restoring vision after lens removal (called "aphakia") are necessarily very thick due to the high power required. Such thick contact lenses are uncomfortable and cannot deliver sufficient oxygen to support long-term ocular health. IOLs are used in the majority of cases to overcome the aforementioned difficulties associated with cataract glasses and contact lenses.

Known IOLs include non-deformable, foldable and expansible lenses, which may be formed from materials such as acrylics, hydrogels or polysiloxanes. These IOLs are implanted by making an incision in the cornea and inserting a preformed IOL. To treat cataracts, the natural lens is removed before the IOL is implanted. In some procedures, the capsule is left in place following lens extraction. The IOL is then implanted inside the capsule via the capsulorhexis; a hole typically of a few mm in diameter made at the anterior capsule surface. The capsulorhexis is made to provide an opening from which the content (cortex and nucleus) of the lens can be removed during the procedure. To minimise trauma during implantation, foldable and expansible IOLs have been developed. These lenses may be rolled up and inserted through a small tube, which allows a smaller incision to be made in the cornea as well as a smaller diameter capsulorhexis to be made in the capsule. Smaller incisions and rhexes provide quicker post-op recovery as well as improved post-op visual outcomes due to less likelihood of distortion of the cornea. For example, dehydrated hydrogels can be used with these small incision techniques. Hydrogel lenses are dehydrated before insertion and naturally rehydrate once inside the capsular bag. To be suitable as IOLs, these deformable lenses require not just appropriate optical properties, but also mechanical properties, such as structural integrity and elasticity, to permit them to deform during implantation and then regain their shape in vivo. However, currently available IOLs are still relatively much more rigid than the young, flexible natural lens. Thus, such IOLs are not capable of accommodating when in vivo, and so are not an optimal solution as they do not restore the near vision capability (accommodation) of the natural young eye.

To further develop IOLs and reduce surgical incisions to below 1.5 mm, techniques utilising injectable IOLs have been suggested. Injectable IOLs would be implanted by lens filling (or refilling) procedures, such as Phaco-Ersatz. In such a procedure the natural crystalline material of the lens is extracted while the lens capsule-zonule-ciliary body framework is maintained. The intact lens capsule is then refilled by injecting a low viscosity material into the empty capsular bag through a small diameter capsulorhexis. The material may then be cured in situ. Injectable IOLs use the capsular bag to form the shape of the lens. Provided the elasticity of the refilling material is sufficiently low, the lens shape can then be manipulated by the ciliary muscles and zonules as occurs with the natural lens. Consequently, such injectable IOLs are able to accommodate in vivo. By replacing the hardened lens material of a presbyopic patient with a soft gel injectable IOL the patient's ability to change focus, or accommodate, can be restored.

Apart from problems with in situ curing, such as controlling the crosslinking process and finding clinically acceptable conditions, there has been a struggle to develop polyorganosiloxane compositions for use as injectable IOLs. Injectable IOL materials need to have a suitable viscosity for injection, a suitable refractive index, suitable mechanical characteristics after curing, i.e. modulus, good transparency, be biocompatible, including having minimal extractables and be sterilisable.

The properties, such as viscosity, modulus and extractables, differ from those required for deformable IOLs. Consequently, materials useful in deformable IOLs are by no means suitable for use as injectable IOLs. For example, polydimethylsiloxane (PDMS) has been employed as a material in foldable or deformable IOLs. In the injectable IOL context though, PDMS has been found to have a relatively low viscosity and thereby a tendency to leak out of the injection site (i.e. the capsular bag) before curing. To address this deficiency, high viscosity polysiloxanes have been added to the PDMS reaction mix. However, a drawback of high viscosity silicones is that they can entrap air bubbles, which can impair the optical quality of the resulting product. Also, they are difficult for a surgeon physically to inject in a very delicate environment, often requiring substantial force. In addition, it has been found that polyorganosiloxanes having a high fraction of dimethylsiloxane units may have an unacceptably low specific gravity with the undesired result that the injected lens material will float on any aqueous layer present in the capsular bag. In such a case, it will be difficult to fill the capsular bag completely and will require the surgeon to manually express intra-capsular water in order to maintain the correct lens shape during the filling and curing process.

Therefore, it is desirable to formulate processes for replacing the natural lens with an accommodating IOL that provides optimal results in vivo. Further, it is desirable to formulate injectable lens forming materials from polysiloxanes that has a suitable refractive index and the desired mechanical and optical qualities so as to constitute an optimal replacement for the natural lens.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

As used herein, the term "comprise" and variations of the term, such as "comprising", "comprises" and "comprised", are not intended to exclude other additives, components, integers or steps.

SUMMARY OF THE INVENTION

When conducting experiments to refill the natural lens with a soft gel, it was surprisingly found that in non-human primates (rhesus) the replacement induced a refractive error (hyperopia) in all animals. Similar results were obtained for experiments conducted with ex vivo human eyes. It was expected that if the contents of the natural lens is replaced with a polymer of the same refractive index (RI) no refractive error would be induced. Conventional optical measurements and modelling provide 'text-book' values for the average refractive index of the natural human lens as being between 1.40 and 1.42.

It has been discovered that, if the lens of an eye is evacuated and the capsular bag refilled with polymers with refractive index in the 'text-book' range for the eye, such as dimethyl siloxanes having an RI of 1.407, the resulting power-load and power-stretch curves show not only an induced refractive change in the eye, but also a departure from the accommodative response (change in power with ciliary muscle effort and change in power with change in lens diameter) of a natural lens. In contrast, when higher refractive index materials are used to refill the lens capsular bag (e.g. RI of 1.4457), the refilled lens very closely mimics the static refractive state and the accommodative response of the natural lens.

Accordingly, the RI of a material for refilling the lens without resulting in a departure from the lens' original optical power has surprisingly been found to be higher than expected, being between 1.421 and 1.450. The RI of a material for refilling the lens of rhesus primates and maintaining its optical power is preferably between 1.426 and 1.444, more preferably between 1.435 and 1.444 and most preferably about 1.440. For humans generally, the RI of a material for refilling the lens without introducing a change in power is typically greater than 1.421 and less than about 1.442. More usually, it is between 1.426 and 1.438. In one embodiment, it is about 1.427. For humans over the age of 40, the RI of a material for refilling the lens without introducing a change in power is typically greater than 1.426 and less than about 1.442. More usually, it is between 1.426 and 1.438. In one embodiment, it is about 1.427.

Consequently, in one aspect, the present invention provides a method of determining the IOL refractive index for an ocular replacement material for replacing tissue in the capsular bag comprising combining a neutral (non-correcting) reference refractive index ("NRRI") of between 1.421 and 1.450 with a refractive index correction factor ("RICF") ascertained by reference to the refractive power required to correct the patient's refractive error (i.e. long-sightedness or short-sightedness). The NRRI has surprisingly been found to be different for rhesus primates and humans, despite other substantial similarities which have led to the rhesus eye being a widely accepted model for the human eye. In this specification, some of the data is based on rhesus eyes, where the NRRI is assessed to be between 1.426 and 1.444, more likely 1.435 and 1.444 and likely to be about 1.440. The NRRI for humans generally is assessed to be between 1.421 and 1.442, more likely between 1.426 and 1.438 and likely to be about 1.427. The NRRI for humans over the age of 40 is assessed to be between 1.426 and 1.442, more likely between 1.426 and 1.438 and likely to be about 1.427.

The refractive power required may be assessed in known ways by optometric examination. The related RICF may be calculated in known ways using suitable formulae.

By adjusting the refractive index of the polymer used to refill the lens capsular bag, one can correct refractive errors (such as myopia and hyperopia). This involves measuring the patient's refractive state and prescribing a material with the correct IOL refractive index to 'neutralise' the refractive condition.

Further, by replacing the hardened material of a presbyopic natural lens with a soft gel having a correct NRRI, accommodation may be restored to a subject suffering presbyopia.

Accordingly, another aspect of the present invention is a method of treating presbyopia of a subject by replacing tissue in the subject's capsular bag comprising the steps of:
(a) obtaining an ocular replacement material having a refractive index equivalent to a neutral (non-correcting) reference refractive index of between 1.421 and 1.450; and
(b) replacing the tissue in the subject's capsular bag with the ocular replacement material.

In step (a), the NRRI is preferably between 1.426 and 1.444 for rhesus primates, more preferably between 1.435 and 1.444, and most preferably about 1.440. For humans generally, the NRRI is desirably between 1.421 and 1.442. More usually it is between 1.426 and 1.438. In one embodiment, it is about 1.427. For humans over the age of 40, the NRRI is desirably between 1.426 and 1.442. More usually it is between 1.426 and 1.438. In one embodiment, it is about 1.427.

A further aspect of the present invention provides a method of treating myopia, hyperopia, or presbyopia of a subject by replacing tissue in the subject's capsular bag comprising the steps of:
(a) calculating a refractive index correction factor based on an estimate of the refractive power correction required, if any, derived by measurement and/or examination of the subject's eye;
(b) determining the sum of the refractive index correction factor of step (a) if any with a neutral (non-correcting) reference refractive index of between 1.421 and 1.450;
(c) obtaining an ocular replacement material having a refractive index of the sum determined in step (b); and
(d) replacing the tissue in the subject's capsular bag with the ocular replacement material.

In step (b), the NRRI is preferably between 1.426 and 1.444 for rhesus primates, more preferably between 1.435 and 1.444, and most preferably about 1.440. For humans generally, the NRRI is desirably between 1.421 and 1.442. More usually it is between 1.426 and 1.438. In one embodiment, it is about 1.427. For humans over the age of 40, the NRRI is desirably between 1.426 and 1.442. More usually it is between 1.426 and 1.438. In one embodiment, it is about 1.427.

Preferably the ocular replacement material of step (c) is an ocular replacement material for replacing tissue in the capsular bag having suitable properties for an accommodating lens. In one embodiment, the ocular replacement material is a siloxane polymer, such as one formed in situ from a cross-linkable siloxane macromonomer. The polymer is desirably polymerisable in situ in the capsular bag. Suitable ocular replacement materials include the polymers described in this specification and co-pending PCT application entitled "Biological polysiloxanes" by Dr T C Hughes et al filed on the same date as this specification and claiming priority from U.S. provisional patent No. 60/796,936.

The material will have a predetermined refractive index calculated to be the sum of (i) the NRRI for rhesus primates, humans generally or humans over the age of 40, as described above, and (ii) a predetermined RICF ascertained by reference to the refractive power required to correct the refractive error. The RICF may be zero e.g. for the case of an emmetropic eye (i.e. an eye not requiring any refractive correction). In preferred embodiments, the predetermined refractive index of the material may be 1.421-1.422, 1.422-1.423, 1.423-1.424, 1.424-1.425, 1.425-1.426, 1.426-1.427, 1.427-1.428, 1.428-1.429, 1.429-1.430, 1.430-1.431, 1.431-1.432, 1.432-1.433, 1.433-1.434, 1.434-1.435, 1.435-1.436, 1.436-1.437, 1.437-1.438, 1.438-1.439, 1.439-1.440, 1.440-1.441, 1.441-1.442, 1.442-1.443, 1.443-1.444, 1.444-1.445, 1.445-1.446, 1.446-1.447, 1.447-1.448, 1.448-1.449 or 1.449-1.450.

In one embodiment, the refractive index of the ocular replacement material is 1.440 when the RICF is 0 (i.e. an NRRI of 1.440) for rhesus primates, and 1.427 for humans.

Preferably, when treating myopia or hyperopia the ocular replacement material used in step (e) results in an accommodating IOL.

In yet a further aspect, the present invention provides an ocular replacement material for replacing tissue in a subject's capsular bag having a refractive index of the sum of: (a) a neutral (non-correcting) reference refractive index of between 1.421 and 1.450; and (b) a refractive index correction factor ascertained by reference to the refractive power required to correct the subject's refractive error, if any.

In a further aspect, the present invention provides an accommodating IOL for replacing tissue in a subject's capsular bag comprising the above described ocular replacement material.

Further, the invention provides a method of producing an ocular replacement material for a subject having ametropia (i.e. a refractive error such as myopia or hyperopia) or presbyopia comprising:
(a) calculating a refractive index correction factor based on an estimate of the refractive power correction required, if any, derived by measurement and/or examination of a subject's eye;
(b) determining the sum of the refractive index correction factor of step (a) if any with a neutral (non-correcting) reference refractive index of between 1.421 and 1.450; and
(c) producing an ocular replacement material having a refractive index of the sum determined in step (b).

The invention also comprises a method of implanting an accommodating IOL comprising introducing an ocular replacement material having a refractive index of the sum of: (a) a neutral (non-correcting) reference refractive index of between 1.421 and 1.450; and (b) a refractive index correction factor ascertained by reference to refractive power required to correct a refractive error into a capsular bag of a subject.

Preferably, the ocular replacement material is curable and the method further comprises the step of curing the ocular replacement material after introducing the ocular replacement material into the capsular bag.

Another aspect of the present invention is the use of an ocular replacement material for replacing tissue in a subject's capsular bag having a refractive index of the sum of: (a) a neutral (non-correcting) reference refractive index of between 1.421 and 1.450; and (b) a refractive index correction factor ascertained by reference to refractive power required to correct a refractive error, for the manufacture of an accommodating intraocular lens for use in treating myopia, hyperopia or presbyopia.

The ocular replacement material of the present invention is preferably a macromonomer having a viscosity before curing of between 1,000 and 150,000 cSt, preferably 1,000 to 80,000 cSt and more preferably 1,000 to 60,000 cSt. Preferably, the ocular replacement material of the present invention is curable into a polymeric material having a modulus at 37° C. of less than 50 kPa, preferably less than 10 kPa and more preferably less than 5 kPa.

In preferred embodiments of the invention, the ocular replacement material is a siloxane macromonomer.

To better illustrate the invention, the invention will now be described with reference to particular embodiments and examples, which do not limit the scope of the invention described.

BRIEF DESCRIPTION OF THE DRAWINGS

In the accompanying figures.

DETAILED DESCRIPTION OF THE EMBODIMENTS

In testing the efficacy of a soft gel for use as an injectable IOL, the inventors conducted experiments on non-human primates (NHP) (rhesus). In these experiments, each subject had the lens of its right eye evacuated and refilled with a soft gel made from a PDMS based polymeric material having an RI of 1.407. The power and amplitude of accommodation of the left, natural lens and right, refilled experimental lens of each subject was then compared at various intervals postoperatively. The amplitude of accommodation of the lenses was tested pharmacologically. In short, subconjunctival administration of pilocarpine induces the eye to accommodate to its near focus, increasing the power of the eye. Refractometry (for measuring the refractive state of the eye), using an auto-refractor, was carried out on each eye before and after pilocarpine administration. The difference in the refractive state of an eye before and after administration of pilocarpine indicates the amplitude of accommodation achieved by the lens.

Figure 1:
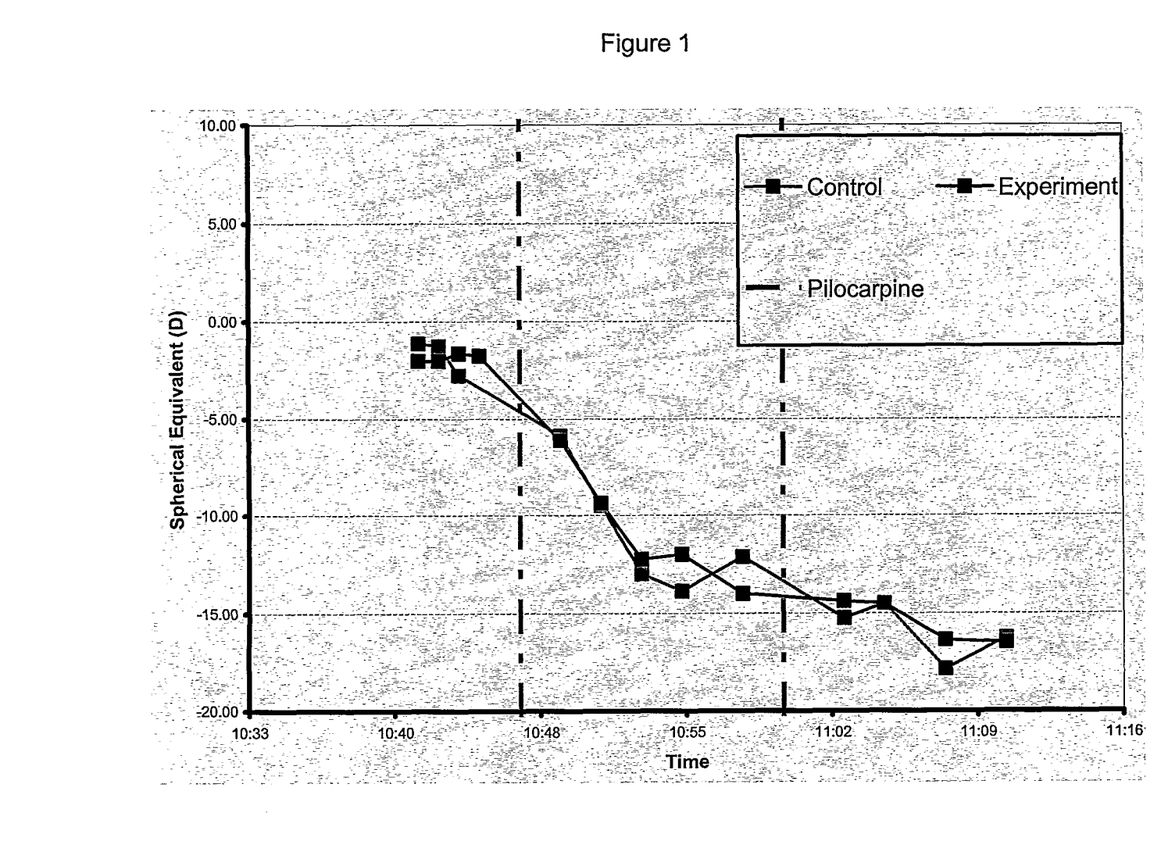
FIG. 1 is a graph of spherical equivalence (i.e. the spherical power component from a measurement of the refractive state of an eye) against time for control and experimental eyes of a NHP (rhesus) subject containing their natural lenses, that is before evacuation and refilling of the experimental eye.

FIG. 1, which is a graph of spherical equivalence against time, shows a comparison of the left (control) and right (experimental) eyes of one NHP subject before the right lens was evacuated and refilled. The spherical equivalence is the mean power of the eye when averaging out the presence of any astigmatism. The control eye is the plot that starts at a marginally higher spherical equivalent at the earliest time (10:40), and the line that starts marginally lower is the experimental eye. The vertical broken lines indicate the times at which pilocarpine is administered to the eyes, inducing accommodation and an increase in power. The increase in power in the eye due to accommodation translates to an apparent myopic-shift of the eye's refractive state. Hence, the spherical equivalence value decreases with increasing amount of accommodation. The two plots are effectively superimposed, which indicates that the refractive state of both the control and experimental eyes containing their natural lenses was consistent before pilocarpine administration. Further, the administration of pilocarpine to the eyes at approximately 10:47 and 11:00 induced similar changes in the refractive state, which indicates that the amplitude of accommodation of each of the eyes were also consistent.

Figure 2:
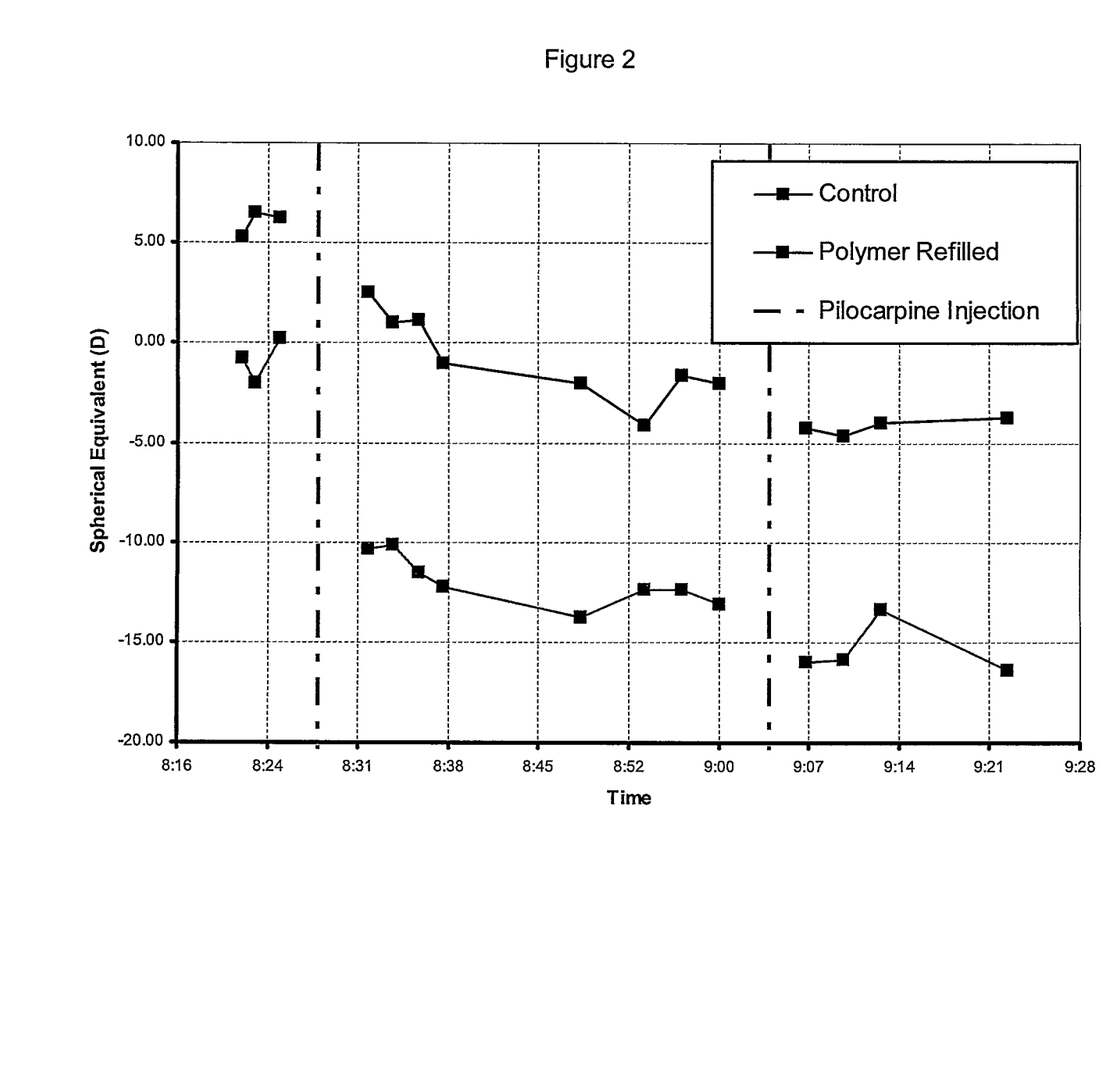
FIG. 2 is a graph of spherical equivalence against time for control and experimental eyes of the NHP (rhesus) subject of FIG. 1 seven days after the lens of the experimental eye was evacuated and refilled with a polydimethylsiloxane (PDMS) based polymeric material having an RI of 1.407.

FIG. 2 shows the response to pilocarpine administration of the control and experimental eyes of the subject of FIG. 1 seven days after evacuation of the lens capsular bag of the experimental eye and injection of a PDMS based polymeric material having an RI of 1.407 to form an accommodating IOL. The upper line represents the experimental eye containing the IOL and the lower line represents the control eye having the natural lens. Again, the vertical broken lines indicate the times at which pilocarpine was administered. The resting (unaccommodated) refraction of the control and experimental eyes of the subject were quite different. The experimental eye has about +6 D higher refraction than the control eye. This indicates that refilling of the lens with the PDMS based polymeric material induces a hyperopic shift of approximately 6 D which means that the experimental eye has less power than the control eye.

The inventors discovered that each of the subjects consistently experienced a hyperopic shift in the refilled experimental eye, which indicates that the PDMS based polymeric lens did not provide sufficient power to restore the lens to its natural power.

Regarding amplitude of accommodation, as shown in FIG. 2, the overall change in the refractive power of the experimental eye following administration of pilocarpine indicates that the refilled lens is capable of accommodating. However, the results from experiments on each of the subjects showed a median relative amplitude of accommodation of only about 60% of that of the control eyes. Accordingly, the amplitude of accommodation achievable by the PDMS based polymeric lens is less than that of the natural lens.

The differences in power and accommodation discovered by the inventors were confirmed using an ex vivo accommodation simulator (EVAS). This machine simulates accommodation using ex vivo lenses. EVAS uses the intact ciliary body and zonules of the cadaver eyes to manipulate the shape of the cadaver lenses, so that accommodation is achieved in the same manner as for a live eye. During manipulation or stretching, the forces on the lens, the refractive power of the lens and the lens diameter (related to the amount of lens stretching) can be simultaneously measured. When a cadaver eye is placed in the EVAS, the power-stretch or power-load curves of the natural lens can be measured. The lens capsular bag can then be evacuated and refilled by injecting suitable macromonomers and remeasured. The macromonomers in the capsular bag can then be cured by photopolymerisation and the power of the cured refilled lens also measured. EVAS tests were conducted on both human and NHP (rhesus) cadaver eyes.

Various NHP (rhesus) and human eyes were tested using the EVAS by measuring the change in power obtained from the lens of the eye as a factor of the increase in load applied to the lens. For each eye, the measurements were taken for the natural lens, the lens capsular bag refilled by an uncured PDMS based polymeric material having an RI of approximately 1.41 and the lens after the PDMS based polymeric material was cured. These tests showed the rate of change of lens power (accommodation or disaccommodation) given a change in the amount of muscular force exerted by the ciliary body and zonules.

Figure 3:
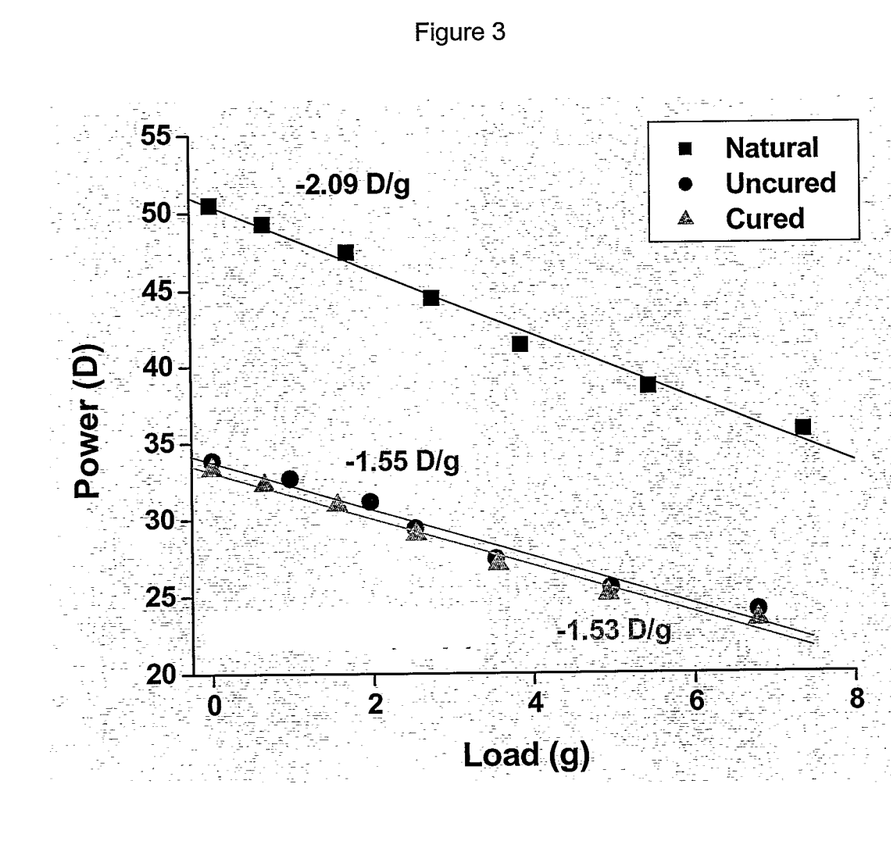
FIG. 3 is a graph of power (D) against load (g) resulting from EVAS testing on an eye containing first its natural lens (natural), second, the lens refilled with uncured PDMS based polymeric material having a refractive index of 1.405 (uncured) and third the lens after the PDMS based material is cured (cured).

The results for a rhesus lens refilled by an uncured PDMS based polymeric material having an RI of 1.405 are given in FIG. 3. The graph shows the work (load) required by the ciliary body/zonules of the eye in order to change the power of each type of lens.

It also shows the difference in power and accommodation resulting from the refilling of the lens capsule. The right-hand extremity of the results (towards a load of 8 g) is analogous to the maximum disaccommodated state of the lens. This represents the resting (unaccommodated) refractive state of the lens. The vertical displacement of the plots at 8 g load shows that the refilled lens (when cured and uncured) has less power than the natural lens at distance focus by approximately 13 D, indicating a hyperopic shift has been induced by refilling. The refilled lens has less power (i.e. is relatively hyperopic) than the natural lens at all loads. The gradients of the lines in FIG. 3 indicate the rate of accommodation of the lens for the same rate of change of ciliary body/zonules load. The gradients of the refilled lenses (−1.55 D/g and −1.53 D/g uncured and cured respectively) are less than that for the natural lens (−2.09 D/g), indicating that the amplitudes of accommodation of the refilled lenses were less than that of the natural lens. These results are consistent with the NHP trials.

Figure 4:
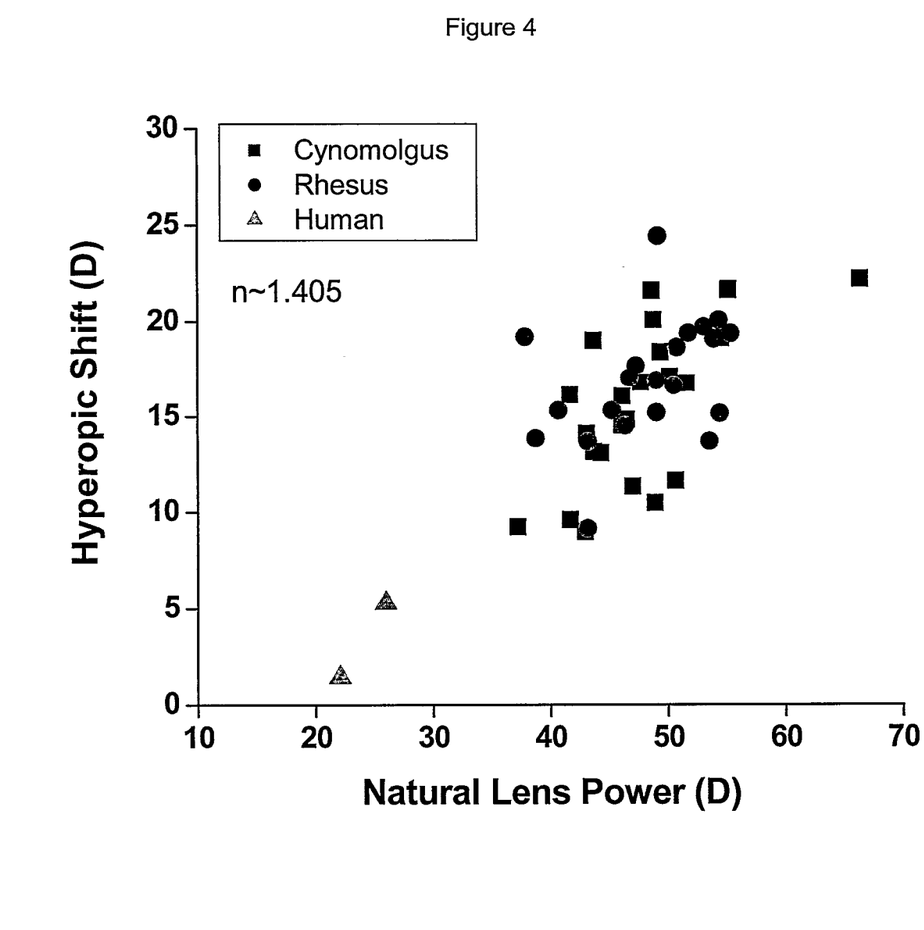
FIG. 4 is a graph of hyperopic shift (D) of various experimental lenses that had been evacuated and refilled with PDMS based polymeric material having a refractive index of 1.405 against the power in dioptres for the initial natural lens measured during EVAS testing.

In addition, the EVAS tests indicated that the results of the NHP (rhesus) trials and tests provide a reasonable predictor for application to the human lens. The graph in FIG. 4 shows an approximately linear relationship between the amount of hyperopic shift attributable to an experimental lens and the power of the initial natural lens. This almost direct correlation between natural lens power and hyperopic shift allows reasonable experimental extrapolation of these principles to humans.

This surprising discovery of an error in the power and amplitude of accommodation of a refilled lens could be attributable to any number of factors including the lens shape, which may be affected by over or under-filling the lens, the post-op corneal shape, the modulus of the PDMS based polymeric material, the refractive index of the PDMS based polymeric material, pupil size and the lack of a gradient refractive index across the refilled lens.

Figure 5:
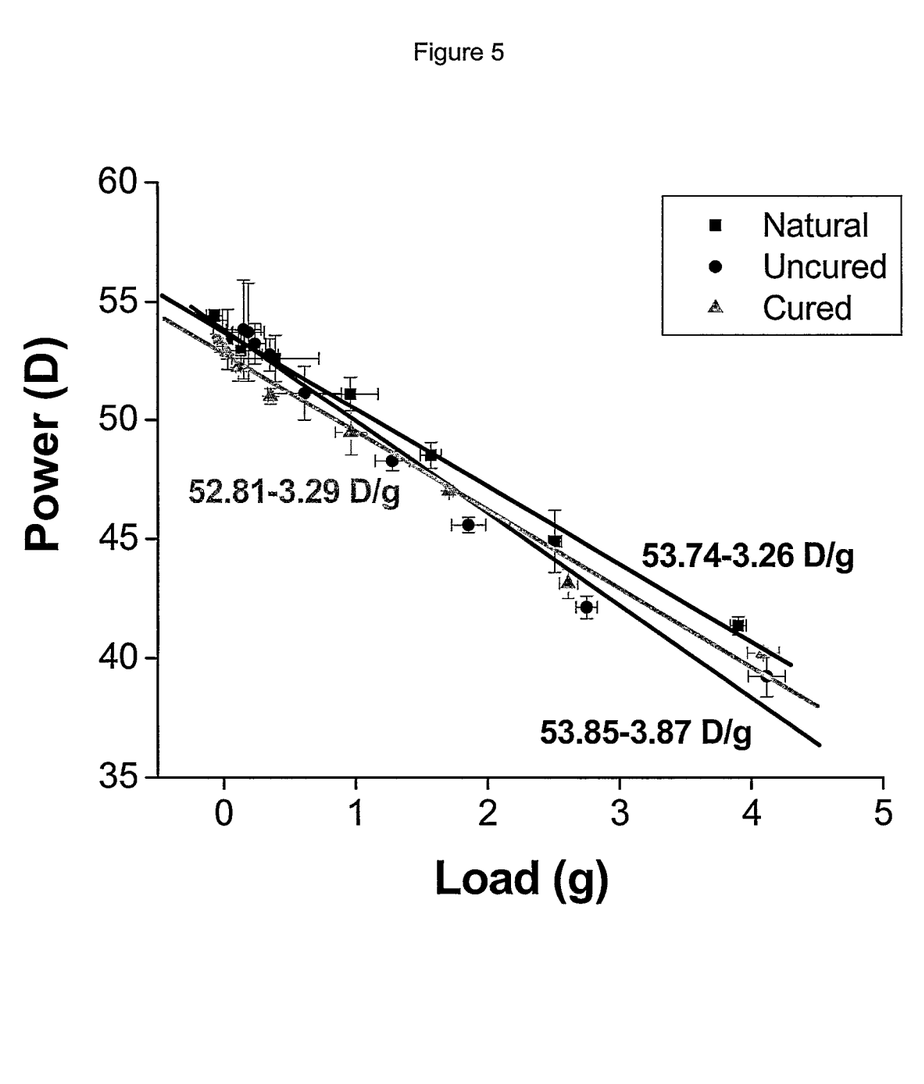
FIG. 5 is a graph of power (D) against load (g) resulting from EVAS testing on an eye containing first its natural lens (natural), second, the lens refilled with uncured siloxane macromer having a refractive index of 1.4457 (uncured) and third the lens after the siloxane macromer is cured (cured).

Without being bound by any theory or mode of action, the cause of the refractive error seen in the primate and EVAS experiments is hypothesised to be due to a mismatch of the refractive index of the PDMS based material, which was approximately 1.41, and the equivalent refractive index required to restore the optical properties (power and accommodation) of the lens to its natural state. This hypothesis is supported by the inventors' discovery that use of a polymeric material having a higher refractive index of 1.4457 produced a lens having similar power and amplitude of accommodation to that of a natural lens. The results of EVAS trials using the higher RI polymeric material are shown in FIG. 5. In this trial an NHP (rhesus) lens was used and measurements were taken for the natural lens, the lens capsular bag refilled by an uncured siloxane based polymeric material having an RI of 1.4457 and the lens after the siloxane based polymeric material was cured. The power of the refilled lens at both distance focus (4 g load) and near focus (0 g load) is approximately equivalent to the power of the natural lens, indicating the higher RI material effectively eliminated the hyperopic shift previously seen in the NHP and EVAS studies using the lower RI materials. Further, the similar gradients of the three plots indicate that the natural, uncured and cured lenses all have similar amplitudes of accommodation.

These results indicate that the refractive index required to restore the power and accommodation amplitude of the lens to its natural state is higher than would be predicted from what is traditionally thought to be the equivalent refractive index of the lens.

Accordingly, the inventors have surprisingly found the NRRI to be between 1.421 and 1.450. The NRRI for rhesus primates is assessed to be between 1.426 and 1.444, more likely 1.435 and 1.444 and likely to be about 1.440. The NRRI for humans generally is assessed to be between 1.421 and 1.442, more likely between 1.426 and 1.438 and likely to be about 1.427. The NRRI for humans over the age of 40 is assessed to be between 1.426 and 1.442, more likely between 1.426 and 1.438 and likely to be about 1.427. These NRRI values may advantageously be used in methods of the present invention for preparing materials for accommodating IOLs that are suitable for use in humans or rhesus primates.

For instance, the NRRI may be used in a method of determining the IOL refractive index for an ocular replacement material for replacing tissue in the capsular bag comprising combining a neutral (non-correcting) reference refractive index of between 1.421 and 1.450 with a refractive index correction factor ascertained by reference to the refractive power required to correct a patient's refractive error.

The refractive power required may be assessed in known ways by optometric examination. For instance, the distance refractive state of a patient may be assessed using conventional methods of refraction, such as subjective refraction (employing e.g. a letter chart and trial frame and trial-lenses of various powers) or an objective refraction, such as retinoscopy, or a more modern auto-refractometer. The near refractive state may be assessed using a near-point chart, or dynamic retinoscopy.

Figure 6:
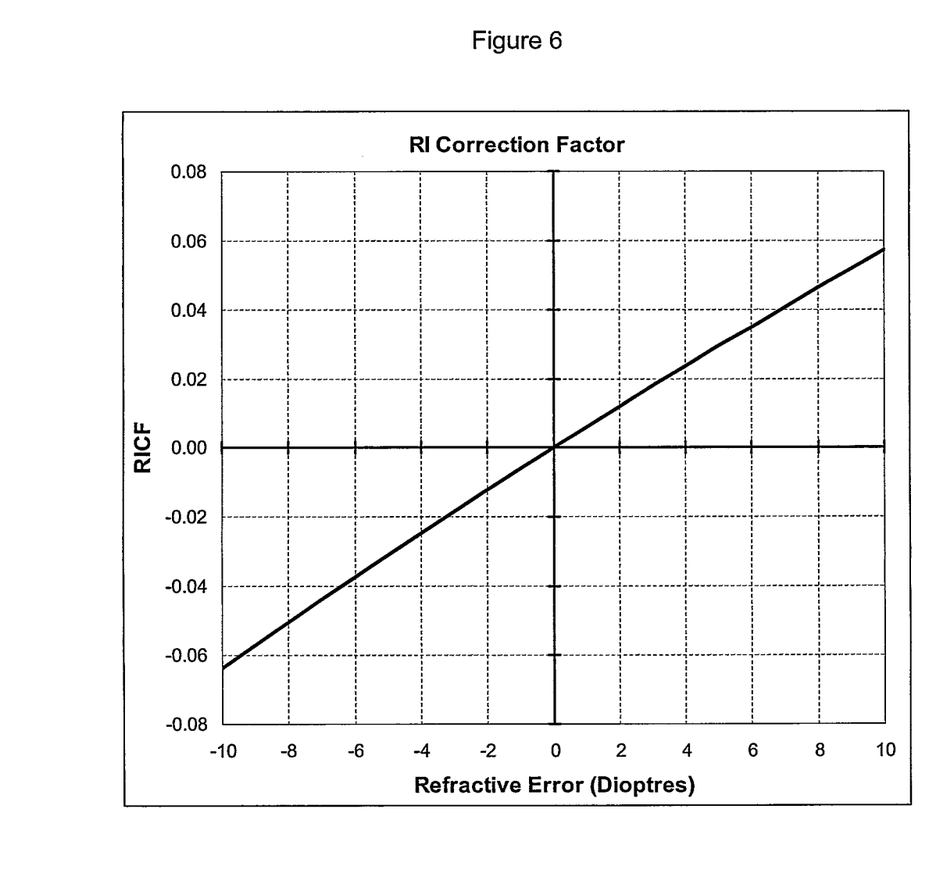
FIG. 6 is a graph relating the refractive index correction factor to the refractive power correction required for one exemplary model.

The related RICF may be calculated in known ways using suitable formulae. For instance, various models may be assumed in order to calculate an RICF from the measured refractive error. One possible model is shown in FIG. 6. It will be understood that any one of a number of different eye models could be used as a basis for calculating the relationship between RICF and refractive error. Further, it will be understood that variation in models would result in slightly different relationships being calculated.

While interpolation of graphs such as that shown in FIG. 6 may be tedious and imprecise in the clinical setting, an approximate rule for calculating RICF based on the same model as shown in FIG. 6 can be defined whereby:

For Myopes: RICF=RX×0.00632

For Hyperopes: RICF=RX×0.00578 where RX is the refractive error to correct in dioptres (D).

As the RICF does not have a linear relationship with refractive error, the rules for myopes and hyperopes differ to afford greater precision.

When used in methods of treating presbyopia, myopia or hyperopia, the ocular replacement material may be introduced into the eye using a lens refilling operation, which is similar many respects to a current cataract extraction and IOL implantation procedure (e.g. extra-capsular extraction procedure). It would be understood how to introduce the material to the eye. For instance, a small corneal incision and a small capsulorhexis are made, through which the lens core (including the cortex and nucleus) are extracted. An ocular replacement material is injected into the intact lens capsule using a fine gauge (e.g. 29-G or finer) cannula and syringe to reform the lens.

Optionally, the ocular replacement material may then be cured, such as by exposure to visible or UV light.

The material used to form the injectable IOL of FIG. 5 was a macromonomer of the structural formula 1

Formula 1 wherein a is 79.1 mol %, b is 20.6 mol % and c is 0.26 mol %.

The macromonomer had the following characteristics:

| | |
|---|---|
| Mw (gpc) | 27120 |
| RI (@ 37° C.) | 1.4457 |
| Viscosity | 8290 cSt |
| Mn | 18274 |
| PD | 1.484 |

The macromonomer of Formula 1 may be synthesised by any suitable method known in the art.

An advantageous method by which the phenyl and methacrylate groups are attached to a siloxane macromonomer is by a hydrosilylation reaction. For instance, using hydrosilylation on a macromonomer that has tri-methyl substituted terminal silicons, the phenyl and methacrylate groups are attached to the siloxane backbone using the allyl-precursors, allyl benzene and allyl-methacrylate, in methods known to those skilled in the art. Scheme 1 illustrates a hydrosilylation reaction.

Scheme 1

The addition of the phenyl and methacrylate groups using hydrosilylation reactions may be either to macromonomers, which are silane functionalized, or to silane functionalized cyclic siloxane intermediates before they are subjected to ring opening polymerisation to form the macromonomer. Suitable cyclic siloxane intermediates include tetramethylcyclotetrasiloxane ($D_4^H$), trimethylcyclotrisiloxane ($D_3^H$), pentamethylcyclopentasiloxane ($D_5^H$) or hexamethyl-cyclohexasiloxane ($D_6^H$).

In the following schemes, where figures such as "a=80, b=20" are provided, these are mol % values for the substituents indicated, and do not necessarily correspond with a, b and c of Formula 1.

One approach is to prepare silane functionalised macromonomer with sufficient silane functionality to allow introduction of both the phenyl groups and the methacrylate groups. For instance, a silane functionalised macromonomer can be sequentially functionalized as depicted in scheme 2.

Scheme 2

Alternatively, a cyclic intermediate monomer is first functionalised with phenyl or methacrylate groups and then subjected to ring opening polymerisation. Scheme 3 shows the synthesis of allyl benzene and allyl methylacrylate functionalised $D_4^H$, which would then by subject to ring opening polymerisation.

preparing the material for the IOL. For a human, an NRRI of about 1.427 would be used as a starting point, and then adjusted or tuned as required.

The following examples, which illustrate how the methods of the present invention may be implemented, are not limiting on the scope of the invention.

Scheme 3

Using the materials and methods of the present invention, a material with a higher (or lower) refractive index may be produced in order to induce a refractive power change in a patient's eye in order to correct a refractive error (resulting in emmetropia) and at the same time produce a gel having a sufficiently low modulus, as described herein, to allow accommodation in vivo. An IOL with increased RI according to the invention as described above can have an NRRI so that there is no shift in an experiment such as illustrated in FIG. 4 for a normal eye. Adjustments can then be made as required in

EXAMPLES

Example 1

A 47 year old patient presents to an eye-care practitioner (e.g. an ophthalmologist) complaining of difficulty with reading and other near visual tasks, such as threading a needle. The distance refractive state of the patient is measured using conventional methods of refraction, such as subjective refraction (employing e.g. a letter chart and trial frame and trial-lenses of various powers) or an objective refraction, such as retinoscopy, or a more modern auto-refractometer as understood by eye-care practitioners. It is found that the patient is emmetropic (i.e. does not require a visual correction to see clearly at distance). However, on near refraction (for example, using a near-point chart, or dynamic retinoscopy), it is found that the patient is experiencing the near vision problems of an early presbyope, resulting from the hardening crystalline lens. In order to treat the presbyopia the patient undergoes a lens refilling operation in order to re-establish a lens (an IOL) which will restore the patient's ability to accommodate.

The lens refilling operation in many respects is identical to a current cataract extraction and IOL implantation procedure (e.g. extra-capsular extraction procedure) with some minor but crucial differences. Hence, the entire procedure is not described in detail as it parallels a procedure currently carried out frequently by ophthalmic surgeons. The differences are described so that technical details may be more fully appreciated.

A small corneal incision is made at the para-limbal region to provide access to the anterior segment. Following dilation of the pupil using a pharmacological agent such as atropine or cyclopentolate, a small capsulorhexis (around 1 mm or less in diameter) is made manually at the periphery of the anterior capsule using fine clawed forceps. Through the small corneal incision and peripheral mini-capsulorhexis, the lens core (including the cortex and nucleus) are extracted. This is carried out using any of a number of implements familiar to ophthalmic surgeons, such as aspirators or small-diameter tipped phaco-probes.

A gel suitable for refilling the capsular bag comprising the macromonomer of Formula 1 is selected which has a refractive index of 1.427, equivalent to the NRRI. This refractive index is the preferred refractive index for this patient as no RICF is required (the patient being emmetropic).

The gel, which includes a benzoin photoinitiator, is injected into the intact lens capsule using a fine gauge (e.g. 27-G or finer) cannula and syringe to reform the lens. The gel is then cured by exposure to light in the visible spectrum. The cured polymer has a modulus of about 5 kPa. Consequently, the still-intact ciliary muscle/ciliary body and zonules of the accommodative apparatus can modify the shape of the injected IOL, thereby restoring accommodation to the patient.

Example 2

Following refraction assessment as described above, it is found that a 62 year old patient has +7.00D of hyperopia. Following slit-lamp biomicroscopic examination, it is observed that the patient also has cataractous changes in the lens which are affecting her vision. Due to the age of the patient, it is deduced that her accommodative amplitude would be very low, being less than about 1D of accommodation. Given the cataractous and advanced presbyopic state of the lens, a lens refilling operation is conducted to replace the cataractous lens with a clear IOL, to restore accommodation to the lens by using a material with a suitable modulus and to correct the hyperopia by selecting a material having an appropriate refractive index.

The refractive index of the material for use in the injectable IOL is calculated in accordance with the present invention. First, an NRRI of 1.427 is selected. Next, the RICF is determined. By referencing the graph of FIG. 6, it can be seen that for a hyperope of +7D, the RICF is 0.0407. Adding the NRRI and RICF gives a final preferred refractive index for the material of the IOL of 1.468.

Alternatively, applying the rule for hyperopia derived from FIG. 6 and described earlier, the +7D hyperopia requires an RICF of 0.0405, resulting in a final preferred refractive index for the material of the IOL of 1.467.

Consequently, a gel suitable for refilling the capsular bag comprising a macromonomer similar to the macromonomer of Formula 1 is selected, which has a refractive index of 1.468.

The gel is injected to form an accommodative IOL using the method described in Example 1. However, a mini-capsulorhexis valve is applied to the capsulorhexis prior to injection of the gel in order to prevent leakage of the uncured macromonomer into the anterior chamber. Following injection and light curing of the polymer gel, the retaining arms of the valve are cut and removed using surgical scissors in order to prevent iris irritation and possibly a subsequent inflammation resulting in an iritis.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method of treating myopia, hyperopia, or presbyopia of a subject by replacing tissue in the subject's capsular bag comprising the steps of:
    (a) determining a refractive index correction factor based on an estimate of the refractive power correction required, derived by measurement and/or examination of the subject's eye;
    (b) determining the sum of (i) the refractive index correction factor of step (a) and (ii) a neutral reference refractive index of between 1.426 and 1.442;
    (c) obtaining an ocular replacement material having a refractive index of the sum of (i) and (ii) determined in step (b); and
    (d) replacing the tissue in the subject's capsular bag with the ocular replacement material.

2. A method according to claim 1 wherein the neutral reference refractive index is between 1.426 and 1.438.

3. A method according to claim 1 wherein the neutral reference refractive index is 1.427.

4. A method according to claim 1 in which the ocular replacement material is a polymer cured in situ from a cross-linkable siloxane macromonomer.

5. A method according to claim 1, wherein the ocular replacement material is curable in situ.

6. A method according to claim 1, wherein the ocular replacement material is shaped by the subject's capsular bag.

7. A method of producing an ocular replacement material for a subject having ametropia or presbyopia, comprising selecting an ocular replacement material having a refractive index determined by summing (i) a refractive index correction factor based on an estimate of the refractive power correction required, derived by measurement and/or examination of the subject's eye and (ii) a neutral reference refractive index of between 1.426 and 1.442.

8. A method according to claim 7 wherein the neutral reference refractive index is between 1.426 and 1.438.

9. A method according to claim 7 wherein the neutral reference refractive index is 1.427.

10. A method according to claim 7 in which the ocular replacement material is a polymer cured in situ from a cross-linkable siloxane macromonomer.

11. A method according to claim 7, wherein the ocular replacement material is curable in situ.

12. A method according to claim 7, wherein the ocular replacement material is shaped by the subject's capsular bag.

13. A method of treating myopia, hyperopia, or presbyopia of a subject by replacing tissue in the subject's capsular bag, comprising replacing the tissue in the subject's capsular bag with an ocular replacement material having a refractive index determined by summing (a) a neutral reference refractive index of between 1.426 and 1.442 and (b) a refractive index correction factor ascertained by reference to refractive power required to correct the patient's refractive error.

14. A method according to claim 13 wherein the neutral reference refractive index is between 1.426 and 1.438.

15. A method according to claim 13 wherein the neutral reference refractive index is 1.427.

16. A method according to claim 13 in which the ocular replacement material is a polymer cured in situ from a cross-linkable siloxane macromonomer.

17. A method according to claim 13, wherein the ocular replacement material is curable in situ.

18. A method according to claim 13, wherein the ocular replacement material is shaped by the subject's capsular bag.

* * * * *